United States Patent

Moss

[11] Patent Number: 5,399,609
[45] Date of Patent: Mar. 21, 1995

[54] MOISTURE INDICATING MOLDING RESINS

[75] Inventor: Arthur Z. Moss, Wilmington, Del.

[73] Assignee: E. I. Du Pont de Nemours and Company, Wilmington, Del.

[21] Appl. No.: 97,415

[22] Filed: Jul. 23, 1993

Related U.S. Application Data

[63] Continuation of Ser. No. 691,208, Apr. 25, 1991, abandoned.

[51] Int. Cl.6 ............................ C08K 3/10; C09K 3/00
[52] U.S. Cl. .................................. 524/423; 524/435; 523/205; 523/206; 252/194; 264/239
[58] Field of Search ............... 524/423, 435; 523/205, 523/206, 221; 252/194; 264/239

[56] References Cited

U.S. PATENT DOCUMENTS

| | | | |
|---|---|---|---|
| 4,018,061 | 4/1977 | Williamitis | 62/125 |
| 4,263,850 | 4/1981 | Bouchard et al. | 102/205 |
| 4,681,576 | 7/1987 | Colon et al. | 604/361 |
| 4,743,238 | 5/1988 | Colon et al. | 604/361 |
| 4,959,445 | 9/1990 | Rosenfeld | 528/181 |
| 5,078,909 | 1/1992 | Shigeta et al. | 252/194 |
| 5,159,005 | 10/1992 | Frandsen et al. | 524/435 |

FOREIGN PATENT DOCUMENTS

| | | |
|---|---|---|
| 308171 | 3/1989 | European Pat. Off. . |
| 400460 | 5/1990 | European Pat. Off. . |
| 2926891 | 1/1981 | Germany . |
| 57-127093 | 7/1982 | Japan . |
| 64-29433 | 1/1989 | Japan . |
| 89201364 | 8/1989 | Japan . |
| 1250480 | 10/1989 | Japan . |
| 0337269 | 2/1991 | Japan . |

*Primary Examiner*—Tae H. Yoon

[57] ABSTRACT

Melt formable thermoplastic resins which exhibit a difference in color between their wet and dry states, processes for melt forming such resins, and the resulting melt formed shaped articles are provided.

23 Claims, No Drawings

MOISTURE INDICATING MOLDING RESINS

This is a continuation of Ser. No. 07/691,208, filed Apr. 25, 1991, now abandoned.

FIELD OF THE INVENTION

The present invention relates to thermoplastic resins, suitable for melt forming, which contain a moisture indicator causing the resins to exhibit a difference in color between the wet and dry states. Also provided are processes for melt forming such compositions into shaped parts, and the shaped parts themselves which also exhibit a color difference between their wet and dry states.

BACKGROUND OF THE INVENTION

It is known in the art that the presence of water is often deleterious when melt forming thermoplastic resins. If sufficient water is present, the steam formed when the resin is heated above 100° C. may cause the resulting part to contain undesirable foam or bubbles. More insidiously, many commercially important resins, such as nylons and polyesters, are chemically degraded by hydrolysis with water, so that the physical properties of the resulting parts are deficient. This is not obvious from simple visual inspection of the part; it usually is detected by destructive testing of the part, or by premature failure of the part in use.

Equipment for drying and conveying resins is expensive to install and maintain, and the necessity for drying resin results in increased costs. It is found in practice that unnecessary costs are sustained when resin is routinely dried, whether or not it actually needs to be, because the moisture level is not known. At times, the drying equipment itself will undetectably malfunction, possibly resulting in humidified rather than dried resin. Certain analytical methods used to test for moisture content depend upon an assumption of homogeneity unlikely to be correct in a large batch of resin which has been exposed to moist air. On-line methods of moisture analysis are very costly.

U.S. Pat. No. 5,078,909 of Shigeta et al. issued Jan. 7, 1992, discloses a moisture-absorbent composition containing a thermoplastic resin and a moisture indicator agent. The compositions have an indicator function having a color variable in accordance with the rate of moisture absorption and can be used to form molded items. No mention is made of control of timing of the color change to correlate with a specific moisture level.

U.S. Pat. No. 4,018,061 issued Apr. 19, 1977, of Williamitis discloses a moisture indicator for refrigerant systems in which a moisture indicating compound, such as a cobalt salt, is mixed with a hygroscopic plastic to indicate when the refrigerant is wet. The mixture is described as being applied from solution as a paint. No mention is made of melt forming mixtures or blends of the plastic and moisture indicator.

U.S. Pat. No. 4,743,238 issued May 10, 1988, and U.S. Pat. No. 4,681,576 issued Jul. 21, 1987, each of Colon et al., describe a hot-melt adhesive containing a moisture indicator, which causes the adhesive to be different colors in the wet and dry states. No mention is made of melt forming shaped parts from the adhesive, which is a complex mixture of polymers, fatty acids, and other adjuvants.

U.S. Pat. No. 4,263,850 issued Apr. 28, 1981, of Bouchard et al., discloses a pyrotechnic cap containing a moisture indicator composition in powdered form of cobalti, cobaltous cyanide and a plastic such as a polyolefin. No mention is made of melt forming shaped parts from the composition, or that the plastic used is hydrolytically unstable.

Japanese Patent 89/201,364, published Aug. 14, 1989, describes a moisture indicating "packet" in which $CoCl_2$ is absorbed by a crosslinked polymer and sealed inside a water permeable plastic bag. By definition, crosslinked resins cannot be melt formed.

Japanese Patent 82/127093, published Jul. 21, 1982, describes a moisture indicating film made from a complex chemical mixture, but eventually involving the reaction of iodate ion with iodide ion in the presence of water to form iodine. The iodine then interacts with starch present to form the colored starch-iodide complex. No mention is made of using this as a molding resin.

U.S. Pat. No. 4,959,445 of Rosenfeld issued Sep. 25, 1990, discloses the polymerization of certain monomers to make aromatic polyesters (polyarylates) in the presence of cobalt salts. The resulting polymers have gray, blue or purple tints, as opposed to polymer which is made without cobalt compounds, which is usually yellow. No mention is made in this patent that these colors are variable or change with the moisture content of the aromatic polyester. No mention is made of adding cobalt compounds to the polyester after the polymerization is completed.

The present invention provides thermoplastic molding resins which exhibit a color change, preferably at or below their critical water concentration, easily determined by simple visual inspection, thereby greatly decreasing the undesirable possibility that wet resin will be melt formed.

The present invention further provides moisture indicator compositions containing a moisture indicator and one or more thermoplastic resins for use in melt forming thermoplastic resins.

The present invention provides methods or processes for melt forming shaped parts or articles from thermoplastic resins containing a moisture indicator.

The present invention further provides a method for monitoring the moisture content of thermoplastic resins for proper melt forming.

The present invention further provides melt formed articles made from thermoplastic resins containing a moisture indicator such that the articles exhibit a color difference between their wet and dry states.

SUMMARY OF THE INVENTION

The present invention provides a resin composition, or moisture warning resin, comprising 1) discrete particles of a moisture indicator composition comprising one or more thermoplastic resins suitable for melt forming shaped articles containing a moisture indicator, and 2) discrete particles of the same or one or more distinct thermoplastic resins, wherein the relative thickness of the moisture indicator composition particles and the resin particles are such that a visual color change occurs in the moisture indicator composition particles at or below the critical water concentration of the resin composition. The one or more resins in component 2) do not contain a moisture indicator.

The present invention also provides a moisture indicating composition comprising one or more thermoplastic resins suitable for melt forming shaped articles containing a moisture indicator, which composition is in the form of discrete particles and exhibits a color change between the wet and dry states of the composition at or below the critical water concentration of the resin.

The present invention further comprises processes for forming shaped articles or parts. One such process comprises a method of using a resin composition to formed shaped articles comprising 1) melting a resin composition comprising a) discrete particles of a moisture indicator composition of one or more thermoplastic resins, suitable for melt forming shaped articles, containing a moisture indicator, and b) discrete particles of the same or one or more distinct plain thermoplastic resins, wherein the relative thickness of the moisture indicator composition particles and the resin particles are such that a visual color change occurs in the moisture indicator composition particles at or below the critical water concentration of the resin composition, 2) shaping the resulting melt or liquid, and 3) cooling the melt or liquid to solidify the composition into a shaped article.

A second such process comprises a method of using a moisture indicating composition to formed shaped articles comprising 1) melting a moisture indicator composition comprising one or more thermoplastic resins, suitable for melt forming shaped articles, containing a moisture indicator, which composition is in the form of discrete particles and exhibits a color change between its wet and dry states at or below the critical water concentration of the resin, 2) shaping the resulting melt or liquid, and 3) cooling the melt or liquid to solidify the composition into a shaped article.

This invention also comprises methods for monitoring the water content of thermoplastic resins prior to melt forming. One such method is for a resin composition comprising discrete particles of one or more thermoplastic resins suitable for melt forming shaped articles mixed with discrete particles of a moisture indicator composition comprising the same or one or more distinct plain thermoplastic resins suitable for melt forming shaped articles containing a moisture indicator, wherein the relative thickness of the moisture indicator composition particles and the resin particles are such that a visual color change occurs in the moisture indicator composition particles at or below the critical water concentration of the resin composition. The method for monitoring the water content of such a resin composition comprises visually inspecting the color of the moisture indicator composition particles in the resin composition, and comparing the color to the colors of the wet and dry states of said moisture indicator composition.

A second method is for a moisture indicator composition comprising one or more thermoplastic resins suitable for melt forming shaped articles containing a moisture indicator, which composition is in the form of discrete particles and exhibits a color change between the wet and dry states of such composition at or below the critical water concentration of the resin. The method for monitoring the water content of such a moisture indicator composition comprises visually inspecting the color of said moisture indicator composition; and comparing the color to the colors of the wet and dry states of said moisture indicator composition.

This invention also comprises shaped articles comprising a melt formed composition of one or more thermoplastic resins containing a moisture indicator, which article exhibits a color difference between its wet and dry states.

DETAILS OF THE INVENTION

Thermoplastics are typically formed by melt forming processes, such as extrusion or injection molding, that is they are melted, and the resulting liquid is formed into the desired shape by a mold or die and then cooled to its solid state, thus forming a shaped part or article. In order to conveniently handle such thermoplastics during melt forming processes, and particularly to feed to the machines in which they will be melted, they are normally in a physical form in which they will gravity flow or be pneumatically transported readily.

The term "particles" as used herein denotes discrete pieces which are readily transported pneumatically or will gravity flow. Regardless of shape, the largest dimension of such particles usually does not exceed about 50 mm and are typically 10 mm or less. The largest dimension usually is not less than about 0.5 mm. The smallest dimension of such particles typically may be about 0.01 mm, although 0.1 mm or greater is preferred. Included within the meaning of particles are pellets, as known by those skilled in the art, flakes, typically flat pieces having a maximum dimension of about 0.05 to about 5 mm and a thickness of about 0.01 to about 0.15 mm; cylinders, typically about 0.5 to about 5 mm in diameter and about 0.5 to about 5 mm long; cubes or rectangular solids, typically about 0.5 mm to about 5 mm on a side; spheres or hemispheres with a diameter of about 0.5 mm to about 5 mm; conical solids; and irregular shapes that flow. Preferably the particles are not in the form of a powder.

The term "critical water concentration" is a practical term which is determined by the requirements of the specific application. It is used herein, when applied to a thermoplastic resin which does not undergo degradation by hydrolysis, to mean the approximate moisture range in a thermoplastic resin at which an unacceptable amount of steam forms when the resin is heated above 100° C. It is used herein, when applied to a thermoplastic resin which undergoes degradation by hydrolysis, to mean the approximate moisture range at which significant chemical hydrolysis of the resin begins. This is usually taken as the range at which the physical properties of the resin are degraded to an unacceptable degree or as the maximum amount of moisture recommended by the supplier. The critical water concentration is specific to a particular polymer or resins. Manufacturers commonly recommend a maximum critical water concentration for particular polymers or resins for use in melt forming shaped articles. Thus such concentrations are widely known and available to those skilled in the art. For example, for a polyamide it is well known to one skilled in the art that a moisture content above 1% is considered too wet for melt forming, and that a moisture content of about 0.5% or less is typically specified. For example, for nylon-6,6 a critical water concentration of less than about 0.3% can be specified for melt forming.

The term "hydrolytically unstable" is used herein to refer to a thermoplastic resin which undergoes degradation by hydrolysis.

The terms "wet" and "dry" states as used herein are relative terms and depend upon the particular use or situation in which the resin is to be utilized. For example, if a hydrolytically unstable resin is to be melt formed, "wet" means above the critical water concentration of the resin, or above the maximum water concentration recommended by the resin manufacturer for melt forming. "Dry" therefore is a moisture level at or below the critical water concentration of the resin, or at or below the maximum water concentration recommended by the resin manufacturer for melt forming.

The term "moisture indicator composition" is used herein to refer to a composition of one or more thermoplastic resins containing a moisture indicator, which composition is in the form of discrete particles and exhibits a visual color change between its wet and dry states.

The term "resin composition" or "moisture-warning resin" is used herein to mean a combination of 1) discrete particles of a composition of one or more thermoplastic resins containing a moisture indicator with which composition exhibits a color change between its wet and dry states, and 2) discrete particles of one or more of the same or different thermoplastic resins. The one or more thermoplastic resins of component 2) in this composition do not contain moisture indicator, and can be the same as or distinct from the thermoplastic resin component in the moisture indicator concentrate of component 1).

The term "plain resin" as used herein denotes one or more thermoplastic resins containing no moisture indicator.

The term "shaped article" or "shaped part" is used herein to describe a thermoplastic resin which has been melt formed into a particular physical shape.

The present invention provides resin compositions and moisture indicator compositions, as defined above wherein the thermoplastic contains or is mixed with a moisture indicator in sufficient concentration so that there is a visual difference in the color of the moisture indicator composition between its wet and dry states. Preferably the color change occurs at or below the critical water concentration of the resin or resin composition. The minimum effective concentration of any particular moisture indicator needed is easily determined with minimal experimentation as defined hereinafter. The moisture indicator herein is a compound or substance that changes color on going from the wet to dry state, and/or vice versa. It is preferred that this color change is reversible. The color may be viewed in visible light or ultraviolet light, but preferrably is visible to the naked eye. It is preferred that the color change is highly noticeable. Any compound or substance that has this property, and can preferably be melt blended with one or more thermoplastic resins is appropriate.

Moisture indicators suitable for use herein may be inorganic salts. Preferred moisture indicators are transition metal salts which form highly colored hydrates, such as cobalt (II) salts. Other hydrate-forming transition metal salts may also be suitable for the practice of this invention, such as copper (II) sulfates. It is important that the colors of the hydrated and anhydrous forms are distinct.

Cobalt salts are particularly preferred. Useful cobalt salts include, but are not limited to $CoCl_2$, $CoBr_2$, $CoI_2$, and $CoSO_4$. Useful concentrations of cobalt salts are from about 0.1 to about 0.01 gram-atoms of cobalt per kg of thermoplastic resin, preferably from about 0.03 to about 0.06 gram-atoms of cobalt per kg of thermoplastic resin.

The moisture indicator composition can be in any physical shape in which it will gravity flow or be pneumatically transported readily as defined above for particles. The physical shape of the moisture indicator or moisture indicator composition can be the same as or different from the plain thermoplastic resin particles.

The moisture indicator may be blended with the thermoplastic resin in many ways, for example solution mixing, with subsequent removal of solvent, or powder blending and compaction (much like powdered metallurgy). Most useful and preferred is melt blending where the resin is melted, as in a screw extruder, mixed within the extruder with the moisture indicator, and the melt formed into particles, in particular pellets. Such pelletizing of resins is well known to those skilled in the art.

The specific shape and composition of the moisture indicator composition will be dictated by the chemical identity of the moisture indicator, the properties of the thermoplastic resins present, and the particular requirements of the application. The following factors need to be considered in choosing a moisture indicator:

- Colors in the wet and dry states (contrasting colors preferred).
- Intensity of the colors (generally the more intense the better. )
- Moisture range at which color change occurs.
- Effect of the moisture indicator on the stability and properties of the thermoplastic resin, especially at elevated (forming) temperatures.
- The rapidity and precision of the color change.
- Ease of mixing with the thermoplastic resin.
- Toxicity
- Cost
- Level of color remaining after part is formed.

The minimum concentration of the moisture indicator needed is inversely proportional to the intensity of the color. If the concentration required is relatively high, there is a greater chance that the moisture indicator will adversely affect the thermoplastic resin properties. The concentration at which this occurs varies depending upon the thermoplastic resin employed and the application in which it is employed. Also, if the color of the moisture indicator is intense, this color may be visible after the part is formed unless other colorants are part of the melt forming mixture.

These problems may be avoided, at least to some extent, by melt forming a resin composition containing 1) a moisture indicator composition of one or more thermoplastic resins containing a moisture indicator, and 2) one or more of the same or a distinct thermoplastic resin which does not contain the moisture indicator. It is normally preferred that the thermoplastic resins used in components 1) and 2) above are the same, since blends of different resins are known to often exhibit unpredictable properties. Thus when the mixture of moisture indicator composition particles and plain resin particles are fed to a screw melter, they are blended, and the concentration of the moisture indicator in the final shaped part is reduced by the weight ratio of the moisture indicator composition particles to the plain resin particles. Thus although it may be desirable to melt form some shaped parts from a moisture indicator mixture or moisture indicator composition without incorporating additional plain resin, generally it is preferred to melt form a composition as defined above.

Reducing the concentration of the moisture indicator in the final shaped part accomplishes several goals. It lessens the chance that the moisture indicator will significantly affect the resin's properties. It may dilute the moisture indicator to the point where it is not visible in the final shaped part. It reduces the cost of the moisture indicator in the shaped part by reducing the amount of moisture indicator used.

Although not critical, it has been found that from about 1 to about 20 percent, preferably from about 3 to about 10 percent of the particles present in the composition for melt forming should contain moisture indicator. This keeps the eventual concentration of the moisture indicator in the shaped part relatively low, while keeping the concentration of moisture indicator composition particles at a high enough level so that they are relatively easily visible. This may vary somewhat, depending on the shape and size of the particles, and the distinctness of the colors of the moisture indicator.

The rapidity of the color change can be influenced by the chemical nature of the moisture indicator. If a quick response to a change in moisture level is required, then a salt which forms a colored hydrate rapidly may be used. If a more gradual response is desired, then the selected moisture indicator should exhibit a slower reaction with water.

An important factor is change of color at or below the critical water concentration of the resin composition. Polymers that are degraded by moisture are believed to have a critical moisture content, a moisture level above which significant degradation of the polymer takes place during melt forming. It is preferred for the moisture indicator composition particles to change color as this moisture level is approached. This is the critical threshold of response, the moisture level at which a response is desired. As those skilled in the art understand, a dry resin particle, for example a 3 mm diameter sphere, a typical size, when initially exposed to moisture, does not have a uniform concentration of water through its cross section. Rather because of diffusion, it will have a higher initial water concentration near the surface than in the interior of the sphere. Thus the overall or average concentration of water in the sphere may reach the critical level before the interior of the sphere has much water in it. In such a circumstance, one can readily understand that a moisture indicator composition particle may not (completely) change color until its average moisture level is well above the critical level.

One solution to this problem is to mix moisture indicator composition particles with plain resin particles. The critical threshold of the response in the resin composition is adjusted by controlling the time it takes for the moisture indicator composition to absorb sufficient water to induce a change in the moisture indicator so that the color change occurs when the average moisture content of the resin composition has reached the critical level. The critical threshold of the response can be controlled by controlling the thickness of the particles of the moisture indicator composition relative to that of the plain resin.

The moisture indicator composition particles can be made of a thickness such that they will become moisture saturated at about the same time as the surrounding thicker plain resin particles reach the critical moisture threshold. Preferably the color change occurs at or below the point when the critical water concentration of the resin composition as a whole is reached. Indeed, the color change threshold of the moisture indicator composition particles in the particle blend can be controlled by varying the thickness of the particle. The thinner the moisture indicator composition particle, the lower the overall water concentration in the resin composition when the moisture indicator composition particles change color, at constant plain resin particle thickness.

The critical water concentration for any given resin is usually known to those skilled in the art, or can be obtained from commercial suppliers of the resin. For any particular plain resin particle size, one can readily determine the moisture indicator composition particle thickness needed as follows. A dry resin composition (containing a moisture indicator composition) is exposed to moisture, and the mixture is observed at intervals of time until the color change is essentially complete. The moisture content of the resin composition is then determined using a moisture analyzer or other standard technique, such as the Karl-Fischer procedure. The particles should change color at or below the point when the critical water concentration is reached. The thickness of the moisture indicator composition particles may be changed to make them more or less sensitive to moisture. Of course the moisture indicator itself must be sufficiently sensitive to moisture to change color before the critical water concentration of the resin is reached.

One convenient method for making relatively thin particles of the moisture indicator composition is to melt blend a thermoplastic resin and moisture indicator in an extruder, and extrude the mixture as a thin sheet or film, and then cut the sheet into flakes. The resin should also be dried according to normal procedures. When the moisture indicator composition is in the form of a film, it is preferably cut to particles of low aspect ratio with a maximum dimension in a range of from about 1.5 to 3 mm. The moisture indicator composition particles are then dry blended with plain resin particles. Any convenient method for achieving dry blending of the components may be used. Tumbling in a container of a volume about 100% greater than that of the blend is satisfactory. If a blend of moisture indicator composition particles and plain resin particles are used, it is preferred that the two types of particles do not separate or settle from each other, as in shipping or storage. Thus as is known to those skilled in the art, the size and shape of the particles should be chosen so that separation is minimized.

It is believed all thermoplastic resins are useful in this invention, but as mentioned above, this invention is particularly useful for thermoplastic resins that degrade in the presence of moisture while being melt formed. Such resins include, but are not limited to, polyacetal, polyamide (nylon, all types), poly(amide-imide), polyarylate, polycarbonate, polyester (all types), and polyurethane. Also included in the meaning of these resins are hybrids such as poly(ester-carbonate) and poly(ester-amide), and various physical forms such as isotropic polyester and liquid crystalline polymer polyester. Preferred resins are polyacetal, polyamide, polyarylate, polycarbonate and polyester. Especially preferred resins are polyacetal, polyamide, polycarbonate and polyester. Most preferred resins are polyacetal; nylon-6,6; nylon-6,12; nylon-6; poly(bisphenol A carbonate); poly(ethyleneterephthalate); poly(butylene terephthalate); and a block copolymer of poly(tetramethyene ether) glycol and poly(butylene terephthalate) .

The particles, particularly the plain resin particles, may contain the usual adjuvants found in moldable thermoplastic resins, such as fillers, colorants, antioxidants, plasticizers, lubricants, tougheners, flame retardants, and the like. These include carbon black, glass fiber, clay or other minerals, and rubber (toughener).

Highly colored particles, whether moisture indicator composition particles or plain resin particles, can present special problems. Obviously, the moisture indicator composition particles cannot contain a colorant that obscures both of the colors they may be, particularly the color that causes it to appear visually different from the plain resin pellets. However, the moisture indicator composition particles may be colored if that color does not interfere with the indicating function. The plain resin particles may be colored, in full or in part, as long as one of the colors of the indicating particles is different from the color of any of the plain resin colored particles. In other words, the color of at least one of the dry state or wet state of the moisture indicator composition particles should be visibly different from the color of all the other particles present.

For example, if all of the plain resin particles were dark blue, the wet form of the moisture indicator composition particles was dark blue, and the dry form of the moisture indicator composition particles was almost colorless (white, if crystallinity is present), one would visibly inspect the particle mixture to find white particles. If they were not visible, the particle blend would be considered wet. If in this example there were yellow colored plain resin particles, the dark blue particles, indicating a wet particle blend, would stand out.

The precision of the color change depends primarily on three factors: 1) homogeneous dispersion of moisture indicator in the moisture indicator concentrate, 2) dimensional uniformity, of the smallest dimension of the moisture indicator composition particles, and 3) homogeneity of dispersion of moisture indicator composition particles in the plain resin particles. Good dispersion of the moisture indicator among the thermoplastic resin requires thorough mixing. This may preferably be accomplished using a typical melt compounding procedure employed for thermoplastic resins, either batch-type or continuous-type. The dimensional uniformity of the smallest dimension of the moisture indicator composition is adjusted by controlling the dimension of the composition particles to the degree required by the application. For example, the dimension can be controlled by fabricating such composition into a film or sheet as illustrated in Example 2. Homogeneous dispersion of the moisture indicator composition particles in the plain resin particles is achieved by any known convenient means. Tumbling has been found to be effective.

The moisture indicator composition of the present invention most preferred comprises discrete particles of nylon-6,6 containing $CoCl_2$. The resin composition of the present invention most preferred comprises 1) discrete particles of a moisture indicator composition comprising nylon-6,6 containing $CoCl_2$, and 2) discrete particles of plain nylon-6,6. The moisture indicator composition contains from about 0 1% to about 10%, preferably from about 0.2 % to about 0.4 %, cobalt by weight. The ratio of moisture indicator composition to plain nylon-6,6 must be such that the color change is visible in the desired application. The moisture indicator composition particles are from about 5 to about 150 micrometers in thickness.

The nylon-6,6 particles and moisture indicator composition particles can be in distinct physical forms. Preferably the nylon-6,6 is in the form of pellets having a cross section of from about 0.1 mm to about 4.0 mm, and the moisture indicator composition is in the form of flakes of about 5 to about 150 micrometers, preferably from about 25 to about 50 micrometers in thickness. The thickness of the flakes is preferably adjusted for the critical water concentration in the resin composition of about 0.3% by weight. If the desired critical water concentration is below 0 3%, then a thinner moisture indicator flake will be needed. Likewise, if the desired critical water concentration is above 0.3%, a thicker flake will be needed.

The present invention further provides processes or methods of using the compositions of the present invention for forming shaped articles. One such process comprises 1) melting a resin composition comprising a) discrete particles of a moisture indicator composition of one or more thermoplastic resins suitable for melt forming shaped articles containing a moisture indicator, and b) discrete particles of the same or one or more different thermoplastic resins, wherein the relative thickness of the moisture indicator composition particles and the resin particles are such that a visual color change occurs in the moisture indicator composition particles at or below the critical water concentration of the resin composition, 2) shaping the resulting melt or liquid, and 3) cooling the melt or liquid to solidify the composition into a shaped article.

A second such process comprises 1) melting a moisture indicator composition comprising one or more thermoplastic resins suitable for melt forming shaped articles containing a moisture indicator, which composition is in the form of discrete particles and exhibits a color change between its wet and dry states, at or below the critical water concentration of the resin, 2) shaping the resulting melt or liquid, and 3) cooling the melt or liquid to solidify the composition into a shaped article.

Typical melt forming techniques useful in the processes of the present invention are injection molding, blow molding, compression molding, and extrusion, which are well known to those skilled in the art. The most common way that thermoplastics are melted suitable for use in these processes is by a screw melter, although other methods, such as melting in a heated cylinder with a ram, are also useful herein. Such processes are described, for example, in the Modern Plastics Encyclopedia, Vol. 65, No. 11 of Modern Plastics, pp. 217–308, (1988), which is hereby incorporated by reference.

Thermoplastic resins and moisture indicators, and their concentrations, suitable for use in the processes of the present invention are as previously described for the compositions of this invention. Also as previously stated, it is preferred to melt form resin compositions comprised of one thermoplastic resin component, and a second component of a thermoplastic resin containing a moisture indicator. Most preferred for use in the processes of this invention are the nylon-6,6 compositions previously detailed.

The present invention further comprises methods for monitoring the water content of thermoplastic resins prior to melt forming processing. One such method is for resin compositions comprising discrete particles of one or more thermoplastic resins suitable for melt forming shaped articles and discrete particles of a moisture indicator composition comprising the same or one or more distinct thermoplastic resins suitable for melt forming shaped articles containing a moisture indicator, wherein the relative thickness of the moisture indicator composition particles and the resin particles are such that a visual color change occurs in the moisture indicator composition particles at or below the critical water concentration of the resin composition. This method comprises visually inspecting the color of the moisture indicator composition particles in the resin composition; and comparing the color to the colors of the wet and dry states of the moisture indicator composition.

A second method is for a moisture indicator composition comprising one or more thermoplastic resins, suitable for melt forming shaped articles, containing a moisture indicator, which composition is in the form of discrete particles and exhibits a color change between the wet and dry states of such composition at or below the critical water concentration of the resin. The method for monitoring the water content of the moisture indicating composition comprises visually inspecting the color of said moisture indicator composition; and comparing the color to the colors of its wet and dry states.

In these methods one or more thermoplastic resins are combined with a moisture indicator, or moisture indicator composition, the composition and particle size of which has been optimized to indicate a visual color change between its wet and dry states. Thus visual inspection of the composition just prior to processing, and comparing the color to the colors of said wet and dry states, indicates whether the resin requires drying to optimize the quality of the melt formed article.

The present invention further comprises melt formed shaped articles made from a mixture or a composition of one or more thermoplastic resins and a moisture indicator, which articles exhibit a color change between their wet and dry states. The color change is preferably reversible. The compositions and processes of the present invention previously described are suitable for use in the composition and preparation of the shaped articles.

The compositions and processes of the present invention are useful for preparing articles from thermoplastic resins of a consistently high quality. Having a means to minimize the chances that the thermoplastic resin will not degrade hydrolytically in melt processing, or will not form steam upon heating, results in fewer deficiencies in the resulting shaped article since the occurrence of such problems can be corrected prior to the melt forming process. The method of the present invention of monitoring the water content of thermoplastic resins prior to melt forming is useful in making melt forming processes more efficient because unnecessary drying of resin and making parts containing hydrolyzed resin can be avoided. The melt formed shaped parts of the present invention are useful in indicating visually their suitability for quality control testing.

EXAMPLES

The invention is further described by the following specific embodiments.

Example 1

Cobalt chloride hexahydrate (0.241 g) was mixed with 68.029 g of ZYTEL ® 101, a commercially available grade of nylon-6,6 from E. I. du Pont de Nemours and Company, Wilmington, Del., in a Haake System 90 batch-type melt mixer set at 260° C., with a melt temperature of 262° C. Mixing proceeded at 15 rpm for about 4 minutes, and 50 rpm for about 8 minutes.

The resultant mixture was a deep royal blue in color, uniform in appearance. The mixture was placed in a heated-platen hydraulic press set at 290° C. and pressed into a film 120–140 micrometers in thickness. The film was blue to turquoise in appearance.

Two pieces estimated to be about 25 cm$^2$ in area each were cut from the pressed film. One of the pieces was placed on the porous plate of a glass desiccator jar beneath which plate was anhydrous $CaSO_4$ desiccant. The other piece of film was placed in a similar jar in which the desiccant had been replaced by a pan of tap water placed below the porous plate, thus creating an atmosphere of 100% relative humidity in the sealed jar.

The desiccant-containing dessicator jar having a low relative humidity will be referred to as the "low RH" jar, and the water-containing jar having a high relative humidity will be referred to as the "high RH" jar.

In just under four hours, the film sample in the low RH jar was observed to have remained turquoise in color, while the film sample in the high RH jar had changed to colorless or faintly pink.

Example 2

In this example, it is shown that a moisture indicator composition can be continuously melt-processed under conditions close to or the same as those found to be effective for plain resin.

Commercially available ZYTEL ® 101 was fed to a 28 mm co-rotating twin-screw extruder manufactured by Werner and Pfleiderer. The extruder screws were equipped with one mixing zone. The extruder was fitted with a vacuum port and an 80 mesh screen pack. The extrudate was fed to a 25.4 cm vertical coathanger film die with a die lip separation of ca. 250 micrometers. The film extruded through the die was quenched on a polished chrome rotating drum, and wound onto a cylindrical core. The melt pressure was ca. 490 psi, the melt temperature was 283° C. The torque on the co-rotating screws, as indicated by the current being delivered to the motor powering the screws, was about 11 amps.

A moisture indicator composition was fabricated by combining 64 g of $CoCl_2.6H_2O$ with 2900 g of ZYTEL ® 101 by shaking in a sealed polyethylene bag. It was observed that significant amounts of the $CoCl_2.6H_2O$ were deposited upon the surface of the bag. The mixture of $CoCl_2.6H_2O$ and ZYTEL ® 101 so produced was fed to the extruder, as described above for plain ZYTEL ® 101. With extruder settings unchanged, the melt pressure was 470 psi, the melt temperature was 280° C., and the screw motor current, 10 amps.

The film fabricated of the moisture-indicating concentrate composition was deep blue and uniform in appearance. By varying the speed of the quench drum films ranging in thickness from 10 to 120 micrometers were fabricated. A total of about 120 m of film was so fabricated. The film was found by atomic absorption spectroscopy to contain 0.36% by weight Co, or $6.1 \times 10^{-5}$ moles Co per gram of polymer.

Samples of the film of the moisture-indicator concentrate composition, about 60 micrometers in thickness, were placed in laboratory desiccator jars in the manner described in Example 1. Within 30 minutes, the specimen in the high RH jar had turned from deep blue to colorless or slightly pink. The specimen in the low RH jar remained unchanged or had turned slightly bluer.

The reversibility of the moisture-indicating effect was demonstrated as well. The two specimens were then switched, that which had become colorless while in the high RH jar now being placed in the low RH jar, and vice versa. Within 15 minutes, the formerly desiccated sample had faded considerably, while the formerly moist sample had taken on a grayish color. After 90 minutes, the formerly desiccated specimen was colorless or slightly gray while the formerly moist specimen was a light grayish blue.

Example 3

Eighty-six g of $CoSO_4.6.5H_2O$ was combined with 3405 g of ZYTEL® 101 by tumbling in glass jars for ca. 16 hours. The mixture was extruded into film as in Example 2. The melt pressure was 750 psi, the melt temperature was 247° C., the screw motor current was 10 amps.

The resulting film was ca. 30 micrometers in thickness, of good quality but exhibiting evidence of incomplete dispersion of the $CoSO_4.6.5H_2O$. The concentration of Co was found by atomic absorption spectroscopy to be 0.22%.

Two specimens of this film were placed respectively in low RH and high RH laboratory desiccator jars as in Example 1. After a few days, the films were examined. The dried film exhibited a faint purple coloration; the moist film was colorless.

Example 4

Seventy-nine g of $CuSO_4.5H_2O$ was combined with 3405 g of ZYTEL® 101 as in Example 3, and fabricated into film 40–50 micrometers thick as in Example 2.

Melt pressure was 660 psi, melt temperature was 245° C. and screw motor current was 9 amps Film was of good quality but exhibited evidence of incomplete dispersion. The concentration of Cu was found by atomic absorption spectroscopy to be 0.06%.

Specimens of the $CuSO_4.5H_2O$-containing film were placed in the laboratory desiccator jars as in Example 3. After a few days, the dried film was a faint cranberry red. The moist film was colorless to yellow.

Example 5

In this example is demonstrated a moisture-warning resin. Film of Example 2, ca. 50 micrometers in thickness was ground into irregularly shaped flakes of ca. 0.5–3 mm in the largest dimension, the aspect ratio of the flakes being on the order of 3 or less.

Twenty and one half g of the ground film flakes were combined with 3176 g of ZYTEL® 101 resin pellets by dry mixing in a polyethylene bag, the flakes and pellets having been dried separately at 80° C. overnight. The bag was shaken until the distribution of film flakes among the resin pellets appeared to be reasonably homogeneous.

The mixture of pellets and ground film was again dried overnight at 70° C. After drying, the mixture was placed in a glass dish inside the low RH desiccator jar in order for the mixture to cool to room temperature. After two hours, a portion of the mixture was transferred to a glass dish in the high RH desiccator jar and sealed within the desiccator jar. The depth of the mixture in the glass dish was ca 1–2 pellet-thicknesses. The glass dish to which the dried and cooled mixture had been transferred had been conditioned overnight in the high RH desiccator jar.

One hour and 28 minutes after the transfer of a portion of the mixture to the high RH desiccator jar, it was observed that the blue flakes in the portion of the mixture in the high RH desiccator jar had almost entirely become colorless, whereas one hour and 13 minutes after the transfer, a number of blue flakes had been visible in the sample.

Water content was determined by the Karl Fischer method. The specimen was held at 150° C. under a dry nitrogen purge for 30 minutes to remove the water and convey it to the Karl Fischer reagent. After the 30 minute hold period, the total water content of the Karl Fischer reagent was determined.

The portion of the mixture which had been retained in the low RH jar exhibited a moisture content no greater than 0.014%. The portion of the mixture which had been held for one hour and 28 minutes in the high RH jar contained 0.2–0.45% moisture with a limited number of the average being about 0.25% moisture.

A moisture content of ca. 0.2–0.4% is held by many familiar with the art of melt processing nylon-6,6 to be a critical level, above which moisture content a significant deterioration in the properties of the processed nylon resin is observed to occur. Thus, this mixture of nylon-6,6 pellets and ground film is a moisture warning resin, with the ground film exhibiting a color change in the critical region.

Example 6

In this example, a moisture indicator composition based upon polyester resin is demonstrated.

A resin consisting essentially of 89% polyethylene terephthalate, about 6% of a copolymer of ethylene and a polar substituted ethylene, and a combination of commercially available processing aids and antioxidants the total of the processing aids and antioxidants being about 5%, was mixed with 50 g of $CoCl_2.6H_2O$ by tumbling. The resin composition, not including the $CoCl.6H_2O$, was fed to the extruder of Example 2. The melt pressure was 410 psi, the melt temperature was 276° C., the extruder torque was 6 amps. The film so fabricated was uniform in appearance though tacky.

When the mixture of the resin composition with $CoCl_2.6H_2O$ was fed to the extruder, the pressure was observed to decrease rapidly, the melt viscosity became very low, and it was not possible to cast a film continuously onto the quench drum. The melt temperature was 270° C. These difficulties notwithstanding, a ca. 450 micron thick piece of sheet or film was obtained. The film or sheet was observed to be quite brittle, and very intensely 'royal' blue in appearance.

A piece of the blue sheet was placed in the low RH jar, while a second piece of the blue sheet was placed in the high RH jar. After a few days, it was observed that the sheet in the low RH jar had remained blue, while that in the high RH jar had become violet. No further change was observed over a period of weeks.

Example 7

In this example is demonstrated a moisture warning resin composition which is similar in processibility and properties to the comparable resin which does not contain the moisture indicator composition.

The moisture warning resin composition of Example 5 was compared with ZYTEL® 101 resin not containing the moisture indicator composition film. Both samples were dried overnight before processing.

Resins were molded on a 6 oz. hydraulic reciprocating screw injection molding machine, using a 3 cavity mold consisting of a 3.2 mm thick×21 cm "dog bone," 16 mm thick and 3 2 mm thick 13 cm long rectangle.

After "lining out" the injection molding machine using the ZYTEL® 101 which did not contain the moisture indicator composition film, 25 "shots" were made under constant conditions. Transition was then made to the ZYTEL® 101 which did contain the moisture indicating composition film. No difference in processing conditions was observed when said moisture-warning resin composition replaced the ZYTEL® 101 not containing the moisture indicator composition film in the injection molding process. After allowing approximately 40 "shots" to complete the transition, an additional 25 "shots" were taken as the test sample. The concentration of Co in the injection molded parts from the moisture-warning resin was found by atomic absorption spectroscopy to be 0.0019%.

The test parts so fabricated from the two test batches were submitted for standard physical tests. The results are shown in Table I.

The few small discrepancies in results between the ZYTEL® 101 and moisture-warning resin composition specimens were thought to be a result of the small number of samples tested.

Example 8

In this example, it is demonstrated that the parts fabricated in Example 7 above are themselves moisture indicating. The parts fabricated from the moisture-warning resin of Example 7 exhibited a blue cast while the parts made from the ZYTEL® 101 not containing a moisture-indicator were pale yellow. The blue bars when placed into the high RH jar were observed over a period of several days to turn yellowish gray.

of the composition at or below the critical water concentration of the resin.

3. The composition of claim 1 or 2 wherein the color difference is reversible.

4. The composition of claim 1 or 2 wherein at least one of the thermoplastic resins degrades in the presence of moisture while being melt formed.

5. The composition of claim 1 or 2 wherein the thermoplastic resin comprises one or more of polyacetal, polyamide, poly(amide-imide), polyarylate, polycarbonate, polyester, or polyurethane.

6. The composition of claim 5 wherein the thermoplastic resin comprises one or more of polyacetal; nylon-6,6; nylon-6,12; nylon-6; poly(bisphenol A carbonate); poly (ethylene terephthalate); poly (butylene terephthalate); or a block copolymer of poly(tetramethylene ether) glycol and poly(butylene terephthalate).

7. The composition of claim 1 or 2 wherein the moisture indicator comprises an inorganic salt.

8. The composition of claim 7 wherein the salt comprises $CoCl_2$, $CoBr_2$, $CoI_2$, $CoSO_4$, or $CuSO_4$.

9. The composition of claim 1 or 2 wherein the moisture indicator composition contains a cobalt salt at a concentration of from about 0.01 to about 0.1 gram-atom of cobalt per kilogram of thermoplastic resin in the moisture indicator composition.

10. A resin composition comprising
1) discrete particles of a moisture indicator composition comprising nylon-6, 6 containing $CoCl_2$, and
2) discrete particles of plain nylon-6,6,
wherein the relative cross section of the moisture indicator composition particles and the nylon-6,6 particles are such that a color change occurs in the moisture indicator composition at or below the

TABLE I

| | Tensile Mod. (kpsi) | Yield Strength (kpsi) | Elong. (%) | Flex Mod. (kpsi) | Flex Strength (kpsi) | Izod Impact (Ftlb/in) | Brittle Point (°C.) | Heat Deflection Temp (°C.) |
|---|---|---|---|---|---|---|---|---|
| Moisture-Indicating | 483 | 11.2 | 45 | 385 | No Break | 1.22 | −58 | 150 |
| Non-Indicating | 487 | 10.7 | 52 | 384 | No Break | 1.22 | −49 | 149 |

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A resin composition comprising
   1) discrete particles of a moisture indicator composition comprising one or more thermoplastic resins, suitable for melt forming shaped articles, containing a moisture indicator, and
   2) discrete particles of the same or one or more distinct plain thermoplastic resins,
   wherein the relative thickness of the moisture indicator composition particles and the resin particles are such that a visual color change occurs in the moisture indicator composition particles at or below the critical water concentration of the resin composition.

2. A moisture indicating composition comprising one or more thermoplastic resins, suitable for melt forming shaped articles, containing a moisture indicator, which composition is in the form of discrete particles and exhibits a color change between the wet and dry states critical water concentration of the resin composition.

11. The resin composition of claim 10 wherein the moisture indicator composition contains from about 0.1% to about 1.0% cobalt by weight.

12. The resin composition of claim 10 wherein the moisture indicator composition particles are from about 5 to about 150 micrometers in thickness, and the plain nylon-6,6 particles have a cross section of about 0.1 mm to about 4.0 mm.

13. The resin composition of claim 10 wherein the moisture indicator composition is different in shape than the plain nylon-6,6 particles.

14. A method of using a resin composition to form shaped articles comprising
   1) melting a resin composition comprising a) discrete particles of a moisture indicator composition of one or more thermoplastic resins, suitable for melt forming shaped articles, containing a moisture indicator, and b) discrete particles of the same or one or more distinct plain thermoplastic resins,
   wherein the relative thickness of the moisture indicator composition particles and the resin particles are such that a visual color change occurs in the moisture indicator composition particles at or below the critical water concentration of the resin composition, 2) shaping the resulting melt or liquid, and
3) cooling the melt or liquid to solidify the composition into a shaped article.

15. A method of using a moisture indicating composition to form shaped articles comprising
   1) melting a moisture indicating composition comprising particles of one or more thermoplastic resins, suitable for melt forming shaped articles, containing a moisture indicator, which composition exhibits a color change between its wet and dry states at or below the critical water concentration of the resin,
   2) shaping the resulting melt or liquid, and
   3) cooling the melt or liquid to solidify the composition into a shaped article.

16. The method of claim 14 or 15 wherein the melt or liquid is shaped by injection molding, blow molding, compression molding, or extrusion.

17. The method of claim 14 or 15 wherein the thermoplastic resin comprises one or more of polyacetal, polyamide, poly(amide-imide), polyacrylate, polycarbonate, polyester, or polyurethane.

18. The method of claim 17 wherein the moisture indicator comprises a cobalt (II) salt or a copper (II) sulfate.

19. The method of claim 14 wherein the moisture indicator composition particles comprise from about 1% to about 20% by number of the resin composition.

20. The method of claim 14 wherein the thermoplastic resin is nylon-6,6 and the moisture indicator composition is nylon-6,6 containing $CoCl_2$.

21. The method of claim 20 wherein the moisture indicator composition particles are from about 5 to about 150 mm in thickness and the plain nylon-6,6 particles have a cross section of about 0.1 mm to about 4 mm.

22. A method for monitoring the water content of a resin composition prior to melt forming processing, said resin composition comprising
   1) discrete particles of a moisture indicator composition comprising one or more thermoplastic resins suitable for melt forming shaped articles containing a moisture indicator, and
   2) discrete particles of the same or one or more distinct plain thermoplastic resins,
   wherein the relative thickness of the moisture indicator composition particles and the resin particles are such that a visual color change occurs in the moisture indicator composition particles at or below the critical water concentration of the resin composition, said method comprising visually inspecting the color of moisture indicator composition particles in the resin composition, and comparing the color to the colors of the wet and dry states of the moisture indicator composition.

23. A method for monitoring the water content of a moisture indicator composition prior to melt forming processing said moisture indicating composition comprising one or more thermoplastic resins suitable for melt forming shaped articles containing a moisture indicator, which composition is in the form of discrete particles and exhibits a color change between the wet and dry states of the composition at or below the critical water concentration of the resin, said method comprising visually inspecting the color of the moisture indicator composition, and comparing the color to the colors of the wet and dry states of the moisture indicator composition.

* * * * *